(12) United States Patent
Bharadwaj

(10) Patent No.: US 7,879,040 B2
(45) Date of Patent: Feb. 1, 2011

(54) METHOD AND APPARATUS FOR OSTEOCHONDRAL AUTOGRAFT TRANSPLANTATION

(75) Inventor: Jeetendra Bharadwaj, Memphis, TN (US)

(73) Assignee: Warsaw Orthopedic, IN ( * ) Notice: Subject to any disclaimer, the term of this patent is extended or adjusted under 35 U.S.C. 154(b) by 670 days.

(21) Appl. No.: 11/551,979

(22) Filed: Oct. 23, 2006

(65) Prior Publication Data

US 2008/0177293 A1    Jul. 24, 2008

(51) Int. Cl.
*A61B 17/58* (2006.01)
*A61B 17/60* (2006.01)
*A61F 2/00* (2006.01)

(52) U.S. Cl. .......................................... 606/89; 606/88

(58) Field of Classification Search ......... 600/564–567; 606/79, 80, 82–85, 86 R, 87–89, 96, 130, 606/167, 170, 172, 176–179; 623/20.16; 83/442, 565, 619

See application file for complete search history.

(56) References Cited

U.S. PATENT DOCUMENTS

| | | | |
|---|---|---|---|
| 5,383,454 A | 1/1995 | Bucholz | |
| 5,782,835 A * | 7/1998 | Hart et al. | 606/79 |
| 5,851,183 A | 12/1998 | Bucholz | |
| 5,871,445 A | 2/1999 | Bucholz | |
| 5,891,034 A | 4/1999 | Bucholz | |
| 5,919,196 A | 7/1999 | Bobic et al. | |
| 5,921,987 A | 7/1999 | Stone | |
| 5,935,128 A * | 8/1999 | Carter et al. | 606/86 B |
| 5,964,805 A | 10/1999 | Stone | |
| 6,007,496 A | 12/1999 | Brannon | |
| D420,132 S | 2/2000 | Bucholz et al. | |
| 6,021,343 A | 2/2000 | Foley et al. | |
| D422,706 S | 4/2000 | Bucholz et al. | |
| 6,110,209 A | 8/2000 | Stone | |
| 6,118,845 A | 9/2000 | Simon et al. | |
| 6,167,145 A | 12/2000 | Foley et al. | |
| 6,190,395 B1 | 2/2001 | Williams | |
| 6,226,548 B1 | 5/2001 | Foley et al. | |
| 6,235,038 B1 | 5/2001 | Hunter et al. | |
| 6,236,875 B1 | 5/2001 | Bucholz et al. | |
| 6,253,210 B1 | 6/2001 | Smith et al. | |
| 6,306,142 B1 | 10/2001 | Johanson et al. | |
| 6,340,363 B1 | 1/2002 | Bolger et al. | |
| 6,348,058 B1 | 2/2002 | Melkent et al. | |
| 6,375,658 B1 | 4/2002 | Hangody et al. | |
| 6,379,302 B1 | 4/2002 | Kessman et al. | |
| 6,381,485 B1 | 4/2002 | Hunter et al. | |

(Continued)

FOREIGN PATENT DOCUMENTS

WO    WO 94/24933    11/1994

(Continued)

OTHER PUBLICATIONS

U.S. Appl. No. 11/508,349, filed Aug. 23, 2006, Bharadwaj.

(Continued)

*Primary Examiner*—Thomas C Barrett
*Assistant Examiner*—Larry E Waggle, Jr.

(57) ABSTRACT

A system for harvesting an implantable graft from the femur of a human having a cartilage overlying a condyle, according to which an overlay extends over the femur and is positioned relative to the femur by an articulating arm assembly.

6 Claims, 2 Drawing Sheets

U.S. PATENT DOCUMENTS

| | | | |
|---|---|---|---|
| 6,395,011 B1 | 5/2002 | Johanson et al. | |
| 6,402,762 B2 | 6/2002 | Hunter et al. | |
| 6,434,415 B1 | 8/2002 | Foley et al. | |
| 6,434,507 B1 | 8/2002 | Clayton et al. | |
| 6,440,141 B1 | 8/2002 | Philippon | |
| 6,470,207 B1 | 10/2002 | Simon et al. | |
| 6,474,341 B1 | 11/2002 | Hunter et al. | |
| 6,488,033 B1 | 12/2002 | Cerundolo | |
| 6,490,467 B1 | 12/2002 | Bucholz et al. | |
| 6,491,699 B1 | 12/2002 | Henderson et al. | |
| 6,535,756 B1 | 3/2003 | Simon et al. | |
| 6,540,668 B1 | 4/2003 | Schulz et al. | |
| 6,553,152 B1 | 4/2003 | Miller et al. | |
| 6,592,588 B1 | 7/2003 | Bobic et al. | |
| 6,636,757 B1 | 10/2003 | Jascob et al. | |
| 6,669,635 B2 | 12/2003 | Kessman et al. | |
| 6,702,805 B1 * | 3/2004 | Stuart | 606/1 |
| 6,708,184 B2 | 3/2004 | Smith et al. | |
| 6,725,080 B2 | 4/2004 | Melkent et al. | |
| 6,754,374 B1 | 6/2004 | Miller et al. | |
| 6,767,354 B2 | 7/2004 | Johanson et al. | |
| 6,796,988 B2 | 9/2004 | Melkent et al. | |
| 6,852,114 B2 | 2/2005 | Cerundolo | |
| 6,892,090 B2 | 5/2005 | Verard et al. | |
| 6,920,347 B2 | 7/2005 | Simon et al. | |
| 6,978,166 B2 | 12/2005 | Foley et al. | |
| 7,007,699 B2 | 3/2006 | Martinelli et al. | |
| RE39,133 E | 6/2006 | Clayton et al. | |
| 7,371,260 B2 * | 5/2008 | Malinin | 623/14.12 |
| 2004/0034437 A1 * | 2/2004 | Schmieding | 623/908 |
| 2004/0039400 A1 | 2/2004 | Schmieding et al. | |
| 2004/0059425 A1 | 3/2004 | Schmieding | |
| 2004/0064193 A1 * | 4/2004 | Evans et al. | 623/23.51 |
| 2004/0176771 A1 | 9/2004 | Schmieding | |
| 2004/0193154 A1 | 9/2004 | Leatherbury et al. | |
| 2005/0101962 A1 | 5/2005 | Schwenke et al. | |
| 2005/0222687 A1 | 10/2005 | Vunjak-Novakovic et al. | |
| 2006/0060209 A1 | 3/2006 | Shepard | |
| 2006/0293682 A1 * | 12/2006 | Justin et al. | 606/88 |
| 2007/0172506 A1 * | 7/2007 | Nycz et al. | 424/422 |
| 2007/0233264 A1 * | 10/2007 | Nycz et al. | 623/18.11 |

FOREIGN PATENT DOCUMENTS

WO    WO 96/11624    4/1996

OTHER PUBLICATIONS

U.S. Appl. No. 11/514,433, filed Sep. 1, 2006, Nycz, et al.

* cited by examiner

US 7,879,040 B2

METHOD AND APPARATUS FOR OSTEOCHONDRAL AUTOGRAFT TRANSPLANTATION

BACKGROUND

This invention relates to an improved osteochondral autograft transplantation procedure and apparatus, and more particularly, to such a procedure and apparatus in which a graft is prepared for a recipient opening.

The human knee consists of three bones—a femur, a tibia, and a patella—that are held in place by various ligaments. The corresponding condyles of the femur and the tibia form a hinge joint, and the patella protects the joint. Portions of the condyles, as well as the underside of the patella, are covered with an articular cartilage, which allow the femur and the tibia to smoothly glide against each other without causing damage.

The articular cartilage often tears, usually due to traumatic injury (often seen in athletes) and degenerative processes (seen in older patients). This tearing does not heal well due to the lack of nerves, blood vessels and lymphatic systems; and the resultant knee pain, swelling, and limited motion of the bone(s) must be addressed.

Damaged adult cartilages have historically been treated by a variety of surgical interventions including lavage, arthroscopic debridement, and repair stimulation, all of which provide less than optimum results.

Another known treatment involves removal and replacement of the damaged cartilage with a prosthetic device. However, prostheses have largely been unsuccessful since they are deficient in the elastic, and therefore in the shock-absorbing, properties characteristic of the cartilage. Moreover, prostheses have not proven able to withstand the forces inherent to routine knee joint function.

In an attempt to overcome the problems associated with the above techniques, osteochondral autograft transplantation, also known as "mosaicplasty" has been used to repair articular cartilages. This procedure involves removing injured tissue from the damaged area and drilling one or more openings in the underlying bone. A graft, or plug, consisting of healthy cartilage overlying bone, is obtained from another area of the patient, typically from a lower weight-bearing region of the joint under repair, or from a donor patient, and is implanted in each opening. It is extremely important that each graft fit in its opening in a precise manner and an embodiment of the present invention involves a technique for advancing the art in this respect.

DETAILED DESCRIPTION

Figure 1:
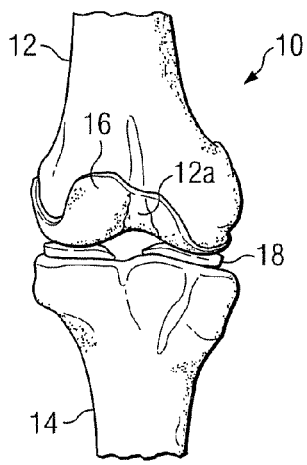
FIG. 1 is an elevational view of a human knee with certain parts removed in the interest of clarity.

Referring to FIG. 1 of the drawing, the reference numeral 10 refers, in general, to a knee area of a human including a femur 12 and a tibia 14 whose respective chondral areas are in close proximity. A cartilage 16 extends over a portion of the chondral area of the femur 12, and a meniscus 18 extends between the cartilage and the tibia. The patella, as well as the tendons, ligaments, and quadriceps that also form part of the knee, are not shown in the interest of clarity.

It will be assumed that a portion of the cartilage 16 extending over the condyle of the femur 12 has been damaged and resected by the surgeon, or has worn away, leaving a damaged area, or defect 12a. It will be also assumed that the surgeon has surgically removed areas of the bone below the damaged cartilage at the defect 12a so as to form an opening that is suited to receive a graft, or grafts. The latter procedure can involve drilling a hole in the underlying bone to a predetermined depth that extends perpendicular to the surface of the femur 12.

Figure 2:
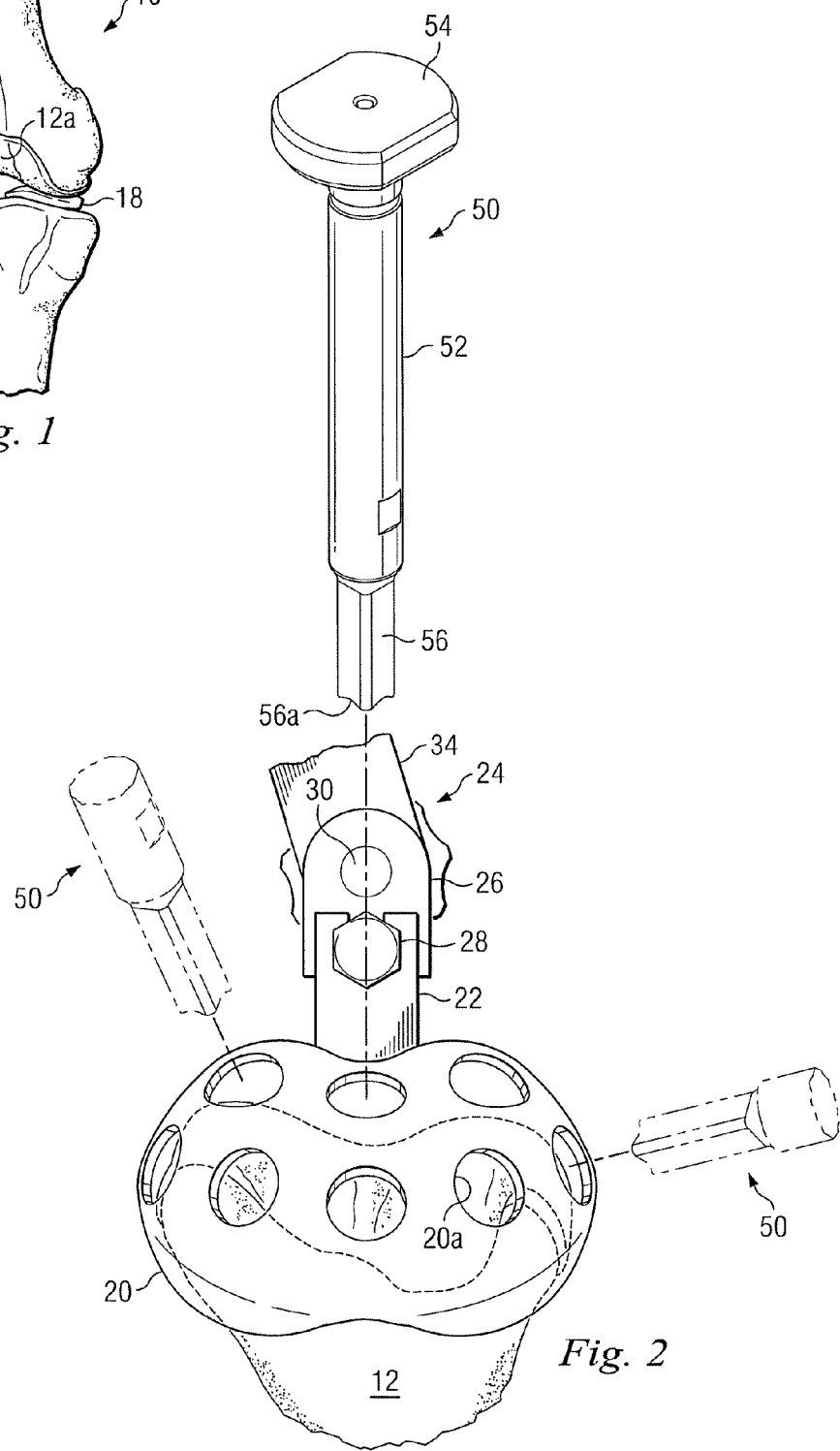
FIG. 2 is an enlarged isometric view of a portion of the knee of FIG. 1 along with a system according to an embodiment of the invention.

Referring to FIG. 2, the femur 12 is shown in an inverted position when compared to FIG. 1, and an overlay 20 extends over the upper surface of the femur, as viewed in the drawing. The overlay 20 can be of a metal or plastic material, and has a series of spaced through openings 20a, with each opening extending perpendicular to the upper surface of the overlay. The curvature of the overlay 20 substantially corresponds to the curvature of the upper surface of the femur 12, it being understood that a plurality of different sized overlays can be provided so that one can be picked that more closely resembles the size and curvature of a particular femur 12. A mounting plate 22 is attached to, or formed integrally with, the overlay 20 and has a U-shaped slot.

An articulating arm assembly 24 is connected to the plate 22, and, to this end, includes a mounting ear 26 mounted to the plate 24 by a bolt 28 that extends through the slot in the plate 22 and into a threaded opening (not shown) in the ear. Thus, the ear 26 can be angularly adjusted relative to the plate 22.

Figure 3:
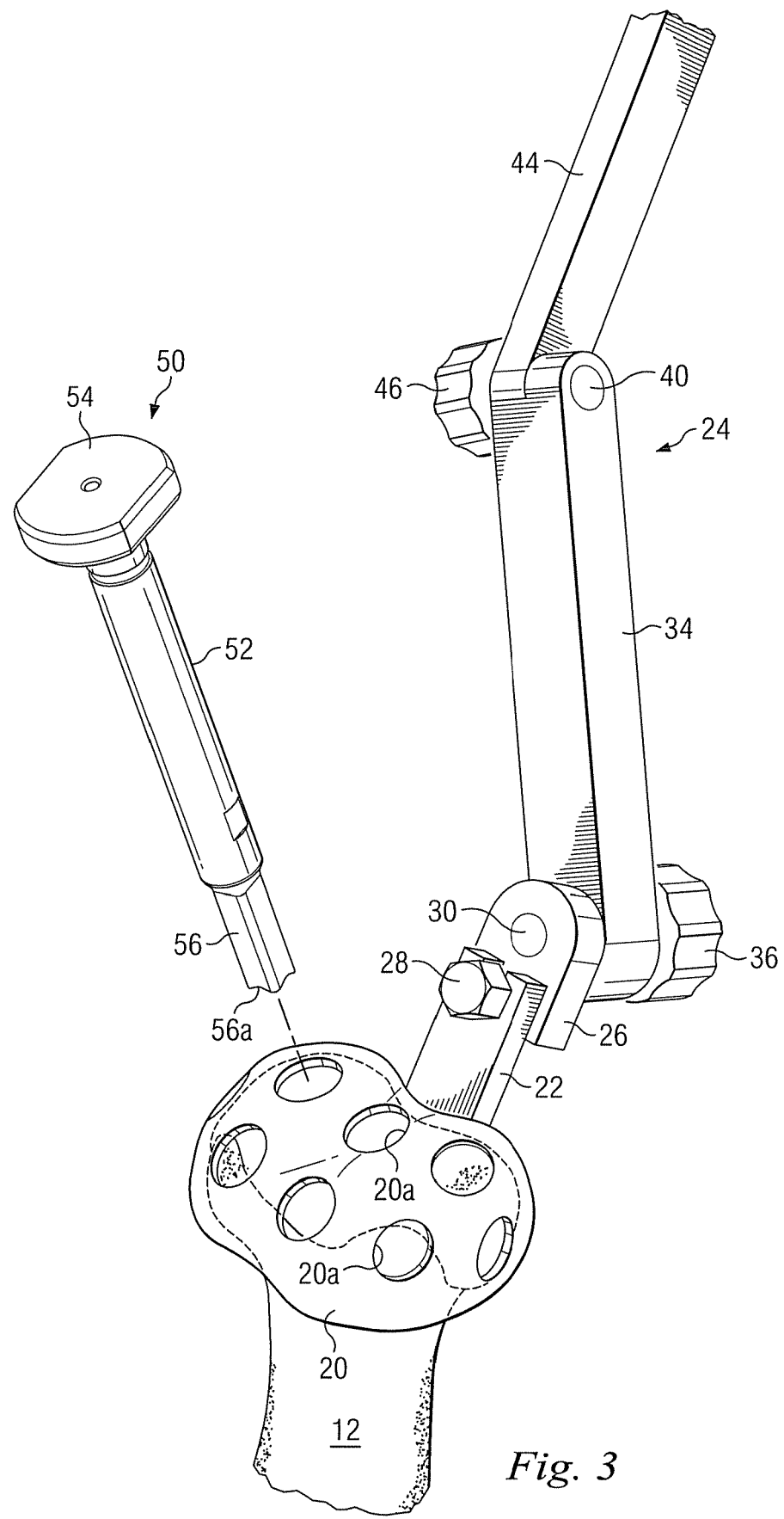
FIG. 3 is a view similar to that of FIG. 2 but depicting additional components of the system of FIG. 2.

Referring to FIGS. 2 and 3, a shaft 30 extends through the ear 26 and through a opening formed through an end portion of an arm 34. A nut 36 is threadedly connected to the other end of the shaft 30 so that the latter end portion of the arm 34 is captured between the ear 26 and the nut 36, and is pivotal about the shaft.

A shaft 40 extends through an opening in the other end portion of the arm 34 and perpendicularly to the shaft 30 to pivotally mount the arm 34 to the shaft. The shaft 40 also extends through an end portion of an arm 44 that rests in a cut-out portion of the arm 34, and a nut 46 is threadedly connected to an end of the shaft 40. Thus, the latter end portion of the arm 44 is captured between the cut-out portion of the arm 34 and the nut 36, and is pivotal about the shaft 40. It is understood that the other end portion of the arm 44 is secured to a support structure, such as a table or the like (not shown).

The arm 34 thus pivots about the shaft 30 in a first plane, and the arm 44 pivots about the shaft 40 in a second plane extending at right angles to the first plane.

The overlay 20 can be manually grasped and adjusted relative to the femur 12 until it extends over the upper surface of the femur 12. Since the curvature of the overlay 20 substantially matches the curvature of the upper surface of the femur 12, the overlay can be positioned substantially parallel to the femur surface utilizing the arm assembly 24, so that the openings 20a extend substantially perpendicularly to the latter surface.

A tool 50 is shown at different positions relative to the overly 20 in FIGS. 2 and 3 and includes a cylindrical body member 52 having a handle 54 disposed at one end, and a hollow tubular member 56 extending from the other end. A relatively sharp, cutting edge 56a is formed at the distal end of the member 56 for cutting a graft from the femur 12, after which the cut graft is forced into the interior of the member 56. It will be assumed that the tool 50 also includes a mechanism for releasing the graft from the member 56. Examples of tools that can be used for cutting, retaining, and/or releasing the graft are disclosed in U.S. patent application Ser. No. 10/792,780, filed on Mar. 5, 2004 (now U.S. publication no. 2004/0176771, published Sep. 9, 2004); U.S. patent application Ser. No. 10/785,388, filed on Feb. 23, 2004 (now U.S. application publication no. 2004/0193154, published Sep. 30, 2004); U.S. patent application Ser. No. 10/984,497, filed Nov. 9, 2004; (now U.S. application publication no. 2005/0101962, published May 12, 2005); U.S. patent application Ser. No. 10/815,778, filed Apr. 2, 2004 (now U.S. application publication no. 2005/0222687, published Oct. 6, 2005); U.S. patent application Ser. No. 08/885,752, filed Jun. 30, 1997 (now U.S. Pat. No. 5,919,196 granted Jul. 6, 1999); U.S. patent application Ser. No. 08/797,973, filed Feb. 12, 1997 (now U.S. Pat. No. 5,921,987 granted Jul. 13, 1999); U.S. patent application Ser. No. 08/908,685, filed Aug. 7, 1997 (now U.S. Pat. No. 5,964,805, granted Oct. 12, 1999); U.S. patent application Ser. No. 08/774,799 filed Dec. 30, 1996 (now U.S. Pat. No. 6,007,496); U.S. patent application Ser. No. 09/187,283, filed on Nov. 5, 1998 (now U.S. Pat. No. 6,110,209, granted Aug. 29, 2000); U.S. patent application Ser. No. 09/425,337, filed Oct. 22, 1999 (now U.S. Pat. No. 6,306,142, granted Oct. 23, 2001); U.S. patent application Ser. No. 09/559,532, filed Apr. 28, 2000 (now U.S. Pat. No. 6,375,658, granted Apr. 23, 2002); U.S. patent application Ser. No. 09/118,680, filed Jul. 17, 1998 (now U.S. Pat. No. 6,395,011, granted May 28, 2002); U.S. patent application Ser. No. 09/624,689, filed Jul. 24, 2000 (now U.S. Pat. No. 6,440,141, granted Aug. 27, 2002); U.S. patent application Ser. No. 09/571,363, filed May 15, 2000 (now U.S. Pat. No. 6,488,033, granted Dec. 3, 2002); U.S. patent application Ser. No. 09/243,880, filed Feb. 3, 1999 (now U.S. Pat. No. 6,592,588, granted Jul. 15, 2003); U.S. patent application Ser. No. 10/004,388, filed Oct. 23, 2001 (now U.S. Pat. No. 6,767,354, granted Jul. 27, 2004); U.S. patent application Ser. No. 10/084,490, filed Feb. 28, 2002 (now U.S. Pat. No. 6,852,114, granted Feb. 8, 2005); U.S. patent application Ser. No. 10/665,152, filed on Sep. 22, 2003 (now U.S. publication no. 2004/0059425, published Mar. 25, 2004); U.S. patent application Ser. No. 10/638,489, filed on Aug. 12, 2003 (now U.S. publication no. 2004/0034437, published Feb. 19, 2004); U.S. patent application Ser. No. 10/443,893, filed on May 23, 2003 (now U.S. publication no. 2004/0039400, published Feb. 26, 2004); and U.S. patent application Ser. No. 10/947,217, filed on Sep. 23, 2004 (now U.S. publication no. 2006/0060209, published Mar. 23, 2006), the disclosures of each of which incorporated herein by reference.

To initiate the harvesting procedure, the overlay 20 is grasped and positioned over the femur 12 until the lower surface of the overlay extends over the upper surface of the femur in a substantially parallel relationship. It is understood that the facing surfaces of the overlay 20 and the femur 12 could be placed in contact, or that the lower surface of the overlay could be slightly spaced from the upper surface of the femur 12. As discussed above, since the curvature of the overlay 20 is designed to substantially match the curvature of the upper surface of the femur 12, and since the overlay is positioned substantially parallel to the femur surface, the openings 20a extend substantially perpendicularly to the latter surface.

The tool 50 is then brought to the vicinity of the overlay 20, and the cutting edge 56a of the member 56 is inserted through one of the openings 20 that extend over an undamaged area of the femur 12. This insures that the member 56 extends perpendicularly to the upper surface of the femur. The tool 50 is then advanced further towards the femur 12 until the cutting edge 56a slices through the layer of cartilage. The manual force is continued and could be increased as necessary so that the cutting edge 56a also cuts through the condyle below the cartilage until the desired depth of cut is attained. The severed graft, including the cartilage and condyle next to the cartilage, enter the hollow, distal end portion of the member 56 and are retained in the latter member. When the desired depth of cut is attained, the tool 50 is manipulated as necessary to completely sever the corresponding end of the condyle thus forming a graft extending in the interior of the member 56. More details of this harvesting process are disclosed in the above identified patent applications.

The harvested graft is then removed from the member 56 and can be implanted in the above-mentioned opening in the defect 12a with the perpendicularity discussed above ensuring that the graft will fit in the defect with a proper fit, and that the contour of the cartilage of the graft will match the contour of the cartilage surrounding the defect.

It is also understood that the system described above can also be used to cut the above-described opening in the defect that receives the graft. In this case, the overlay 20 would be manipulated over the femur 12 until an opening 20a in the overlay would extend over the defect 12a. Then a drill, or other cutting tool, that could include the tool 50, would be inserted through the opening 20a and used to cut the opening.

It is understood that, during the above harvesting procedure, any of the meniscus 18 (FIG. 1) or related tendons, ligaments and quadriceps are removed or pushed aside as necessary to permit access to the above area to permit the harvesting of the graft and/or the cutting of the opening, and/or the implantation of the graft.

It is also understood that an image guiding system, such as the one disclosed in the assignee's U.S. patent application Ser. No. 11/508,349 can be used to assist in positioning the tool 20 relative to the femur 12 during the above procedure.

VARIATIONS

1. The harvesting, the defect preparation, and the implantation can be done with separate tools or with the same tool.

2. More than one graft can be harvested from, and/or more than one defect can be cut in, the femur using the system and procedure discussed above.

3. The graft discussed above can be harvested or prepared from another area of the patient/recipient, from another human, or from any number of anatomic sites, animal or otherwise.

4. The configuration of the cutting edge 56a of the member 56 of the tool 50, including its cross sectional shape, can be varied.

5. The spatial references mentioned above, such as "upper", "lower", "under", "over", "between", "outer", "inner" and "surrounding" are for the purpose of illustration only and do not limit the specific spatial orientation or location of the components described above.

6. The present invention is not limited to use with knees of humans but rather is applicable to other damaged areas of all animals.

7. The method and device disclosed above can be used in any surgical or experimental situation (animal species or otherwise) to harvest grafts or cut openings in any anatomic region.

Those skilled in the art will readily appreciate that many other variations and modifications of the embodiment described above can be made without materially departing from the novel teachings and advantages of this invention. Accordingly, all such variations and modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A system for harvesting an implantable graft from the femur of a human having a cartilage overlying a condyle, the system comprising:
   an overlay having a shape generally corresponding to the shape of the femur and having a series of at least three through openings being independent and spaced apart in a configuration to facilitate selective cutting with a tool;
   wherein said openings are configured to have a size and shape substantially matching the cross-sectional perimeter of the tool; and
   an articulating arm assembly connected to the overlay to permit the overlay to be extending and fixated over the surface of the femur in a substantially parallel relation so that the tool can be inserted through one of the openings along an axis perpendicular to the opening and cut a graft from the femur.

2. The system of claim 1 wherein one arm of the assembly is connected to the overlay and wherein another arm of the assembly is connected to a structure.

3. The system of claim 1 further comprising a mounting plate extending from the overlay and adapted to be connected to an arm of the assembly.

4. The system of claim 1 wherein the assembly comprises a first arm pivotally mounted relative to the overlay about a first axis, and a second arm pivotally mounted relative to the first arm about a second axis extending perpendicularly to the first axis.

5. The system of claim 4 further comprising a mounting plate extending from the overlay, and connected to the first arm.

6. The system of claim 5 further comprising a mounting ear connected to the plate and a shaft connected to the mounting ear about which the first arm pivots.

* * * * *

UNITED STATES PATENT AND TRADEMARK OFFICE
CERTIFICATE OF CORRECTION

| | | |
|---|---|---|
| PATENT NO. | : 7,879,040 B2 | Page 1 of 1 |
| APPLICATION NO. | : 11/551979 | |
| DATED | : February 1, 2011 | |
| INVENTOR(S) | : Bharadwaj | |

It is certified that error appears in the above-identified patent and that said Letters Patent is hereby corrected as shown below:

On the Title Pg, Item (73), under "ASSIGNEE", Line 1, delete "IN" and insert -- Inc., Warsaw, IN (US) --, therefor.

Signed and Sealed this
Fifth Day of April, 2011

David J. Kappos
*Director of the United States Patent and Trademark Office*